United States Patent [19]

Murai et al.

[11] 4,117,159

[45] Sep. 26, 1978

[54] PHARMACEUTICALLY ACTIVE DELTA8-DIHYDROPIMARAMIDE DERIVATIVES

[75] Inventors: Hiromu Murai, Otsu; Yukio Fujita, Takatsuki; Tamiki Mori, Yokaichi; Hiroshi Enomoto, Kameoka; Yoshiaki Yoshikuni, Kameoka, all of Japan

[73] Assignee: Nippon Shinyaku Co., Ltd., Kyoto, Japan

[21] Appl. No.: 768,052

[22] Filed: Feb. 14, 1977

[30] Foreign Application Priority Data

Feb. 26, 1976 [JP] Japan .................................. 51-20870

[51] Int. Cl.$^2$ ..................... A61K 31/24; C07C 103/37

[52] U.S. Cl. ............................. 424/309; 260/557 B; 424/310; 424/324; 560/41; 560/46; 560/47; 560/48

[58] Field of Search ........................ 424/324, 309; 260/557 B; 560/41, 48

[56] References Cited

U.S. PATENT DOCUMENTS

| | | | |
|---|---|---|---|
| 3,281,453 | 10/1966 | Weil et al. | 260/557 B |
| 3,869,506 | 3/1975 | Shen et al. | 260/557 B |

*Primary Examiner*—Leonard Schenkman
*Attorney, Agent, or Firm*—Jacobs & Jacobs

[57] ABSTRACT

N-Phenyl and N-benzyl $\Delta^8$-dihydropimaramides are antiphlogistic and serum cholesterol lowering agents. The compounds, of which N-(2-ethylphenyl)-$\Delta^8$-dihydropimaramide is a representative embodiment, are prepared from reactive derivatives of $\Delta^8$-dihydropimaric acid and the appropriate amine.

7 Claims, No Drawings

PHARMACEUTICALLY ACTIVE DELTA8-DIHYDROPIMARAMIDE DERIVATIVES

This invention relates to $\Delta^8$-dihydropimaramide derivatives expressed by the following general formula:

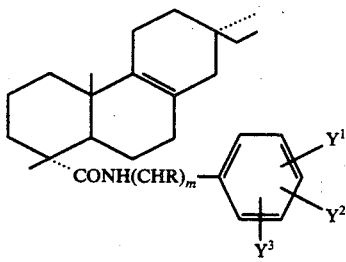
(I)

wherein
R is hydrogen or lower alkyl;
m is an integer of 0 or 1; and
$Y^1$, $Y^2$ and $Y^3$ represent hydrogen, straight or branched lower alkyl or lower alkoxy, carboxyl, carbo(lower alkoxy), hydroxy, trihalogenomethyl, or halogen, $Y^1$, $Y^2$ and $Y^3$ being the same or different.

The compounds of this invention are novel and have antiphlogistic and serum cholesterol level lowering action, and are particularly useful in the therapy of atherosclerosis.

The compounds of this invention can be produced by various synthetic methods. A typical example involves the treatment of a reactive intermediate of $\Delta^8$-dihydropimaric acid such as for example, an acid halide or an acid anhydride, preferably a $\Delta^8$-dihydropimaroyl halide, with from one to three molar equivalents of an amine of the formula:

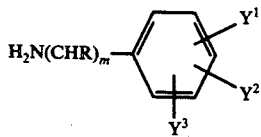
(II)

wherein R, $Y^1$, $Y^2$ and $Y^3$ are as defined above.

Good results can be obtained by using 1 to 1.5 times the molar quantity of an acid acceptor as for example an inorganic base such as alkali carbonate or hydroxide, a tertiary organic base such as N-dialkylaniline or triethylamine. The reaction can be carried out with cooling or heating or at room temperature as necessary, and is usually completed within 1 to 10 hours. Generally the reaction advances quickly at room temperature or under water cooling and is usually completed within three hours. The completion of the reaction can be easily observed from reduction to disappearance of the starting material components on the silica gel thin-layer chromatography. After the completion of the reaction, the desired $\Delta^8$-dihydropimaramide derivatives can be separated from the reaction mixture and further purified according to known methods.

In case of using a reacting water miscible solvent such as acetone, the corresponding reactant is separated in addition to a great quantity of water (usually 10 to 20 times as much quantity of water) to obtain the desired crude product.

In case of using a water immiscible solvent such as benzene, toluene, xylene, n-hexane or chloroform, the reaction solution is first washed with dilute mineral acid and then with water. Then the organic phase is dried as with anhydrous sodium sulfate or magnesium sulfate, filtered, and the filtrate concentrated to produce the $\Delta^8$-dihydropimaramide derivative.

The product can be further purified by recrystallization from a suitable solvent such as methyl alcohol or acetone, or by passage over a silica gel column, eluting with benzene.

The starting material can be obtained from pimaric acid. Pimaric acid (IV) is present in relatively high concentrations in pine resin. The acid, without isolation from the resin, is converted into an inorganic alkali salt such as sodium salt. This salt is then reduced with a suitable reducing catalyst such as Raney Nickel to yield the $\Delta^{8(14)}$-dihydropimaric acid. The $\Delta^{8(14)}$-dihydropimaric acid can be easily purified by recrystallization from organic solvent such as decalin, and the double bond is then isomerized with hydrogen chloride or the like to form $\Delta^8$-dihydropimaric acid (III), which can be further purified by recrystallization. Commercially available reduced pine such as Stabelite rosin can also be subjected to isomerization with hydrogen chloride as above.

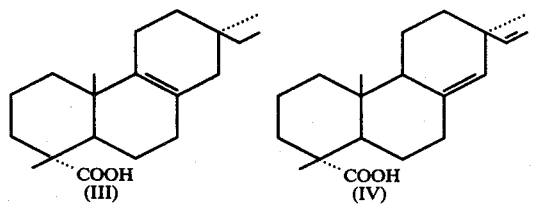

The starting acid (III) is a very stable and inexpensive compound which is easy to obtain. Preparation of reactive intermediates such as $\Delta^8$-dihydropimaric anhydride or $\Delta^8$-dihydropimaroyl halide can be accomplished with ease according to normal methods. The $\Delta^8$-dihydropimaric anhydride can be obtained by using a dehydrating agent such as acetic anhydride or acetyl chloride, while preparation of $\Delta^8$-dihydropimaroyl halide can be attained with ease by using a halogenating agent such as $PX_5$, $PX_3$ or $SOX_2$ where X is halogeno, preferably chloro.

The amines of formula II include aniline; 2,6-dimethylaniline; 2,4-dimethylaniline; 2,4,6-trimethylaniline; 2-methylaniline; 4-methylaniline; 2-ethylaniline; 2,6-diethylaniline; 2,6-diisopropylaniline; m-anisidine; o-anisidine; o-phenetidine; p-phenetidine; 3,4-dimethoxyaniline; p-aminosalicyclic acid and its alkyl esters; p-aminobenzoic acid and its esters; ring-substituted anilines such as trifluoromethylaniline; 3-chloro-2-toluidine; 3-bromoaniline; 3,4-dichloroaniline or 2,6-dichloroaniline; ring-substituted benzylamines such as 2-methylbenzylamine; 4-methylbenzylamine; 3-methylbenzylamine; 2-methoxybenzylamine; 2-chlorobenzylamine; 3-chlorobenzylamine and 4-chlorobenzylamine; as well as α-lower alkylbenzylamine derivatives such as α-ethylbenzylamine; α-methylbenzylamine and 1-phenylhexylamine. Preferably alkyl and alkoxy groups will contain 1 to 3 carbon atoms.

These pimaramide derivatives are generally administered orally at daily dosages of from about 1 to about 100 mg/kg. Although they can be administered parenterally, oral pharmaceutical forms are preferred. These include solid and liquid oral unit dosage forms such as tablets, capsules, powders, suspensions, solutions, syrups and the like, including sustained release preparations. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The invention of this application is now described in further detail by way of examples thereof, but is in no way subject to restriction thereby:

EXAMPLE 1

0.6 ml of triethylamine, 0.5 g of o-ethylaniline (4.2 millimoles) and 5 ml of acetone are mixed, and this mixed solution is agitated while cooling with ice. Added to this mixture under agitation is a solution prepared by dissolving crude $\Delta^8$-dihydropimaroyl chloride [produced from excess thionyl chloride and 1.0 g (3.3 millimoles) of $\Delta^8$-dihydropimaric acid] in 5 ml of acetone. After stirring for 3 hours, the reaction solution is poured into 30 ml of 5% diluted hydrochloric acid and the separated crystals are collected by filtration and washed with water. After drying, the product is crystallized from ethyl acetate and then further recrystallized from the same solvent, followed by filtration and drying. There is resultantly obtained 1.27 g of N-(2-ethylphenyl)-$\Delta^8$-dihydropimaramide as colorless scales.

Yield: 87%, melting point: 139° – 141° C.

| Elemental analysis: $C_{28}H_{41}ON$ | | C | H | N |
|---|---|---|---|---|
| Calcd. | (%): | 82.50 | 10.14 | 3.44 |
| Found | (%): | 82.55 | 10.16 | 3.47 |

Infrared absorption spectrum:
IR $\lambda_{max}^{KBr}$ (cm$^{-1}$): 3330, 1640

The following compounds are produced in a similar way:

| Name of compound | Melting points |
|---|---|
| $\Delta^8$-dihydropimaranilide | 125 – 128° C |
| N-(2,6-dimethylphenyl)-$\Delta^8$-dihydropimaramide | 181 – 184° C |
| N-(2,4,6-trimethylphenyl)-$\Delta^8$-dihydropimaramide | 207 – 210° C |
| N-(2,6-diisopropylphenyl)-$\Delta^8$-dihydropimaramide | 252 254 C |
| N-(4-ethoxyphenyl)-$\Delta^8$-dihydropimaramide | 118 – 122° C |
| N-(2-methyl-5-chlorophenyl)-$\Delta^8$-dihydropimaramide | 203 – 205° C |
| N-(3-trifluoromethylphenyl)-$\Delta^8$-dihydropimaramide | 159 – 162° C |
| N-(3-hydroxy-4-carboxyphenyl)-$\Delta^8$-dihydropimaramide | 252 – 254° C (dec.) |
| N-(4-methoxycarbophenyl)-$\Delta^8$-dihydropimaramide | 70 – 73° C |
| N-(3,4-dichlorophenyl)-$\Delta^8$-dihydropimaramide | 194 – 196° C |
| N-α-n-pentylbenzyl-$\Delta^8$-dihydropimaramide | 121 – 124° C |

In addition, the following compounds are prepared in the same fashion:

| Name of Compound | Appearance and IR Spectra | | |
|---|---|---|---|
| N-α-methylbenzyl-$\Delta^8$-dihydropimaramide | Oil, IRλ | film max (cm$^{-1}$) | 3370 1640 |
| N-(4-methoxybenzyl)-$\Delta^8$-dihydropimaramide | Oil, IRλ | film max (cm$^{-1}$) | 3350 1630 |
| N-benzyl-$\Delta^8$-dihydropimaramide | Oil, IRλ | film max (cm$^{-1}$) | 3370 1630 |
| N-(4-methylbenzyl)-$\Delta^8$-dihydropimaramide | Oil, IRλ | film max (cm$^{-1}$) | 3370 1630 |
| N-(2-chlorobenzyl)-$\Delta^8$-dihydropimaramide | Oil, IRλ | film max (cm$^{-1}$) | 3380 1645 |
| N-α-ethylbenzyl-$\Delta^8$- | Oil, IRλ | (cm$^{-1}$) | 3375 |

| Name of Compound | Appearance and IR Spectra | | |
|---|---|---|---|
| dihydropimaramide | | max | 1645 |
| | Glass, | film | 3360 |
| N-(3-methoxyphenyl)-Δ⁸-dihydropimaramide | IRλ | (cm⁻¹) | |
| | | max | 1650 |

What is claimed is:

1. A compound of the formula:

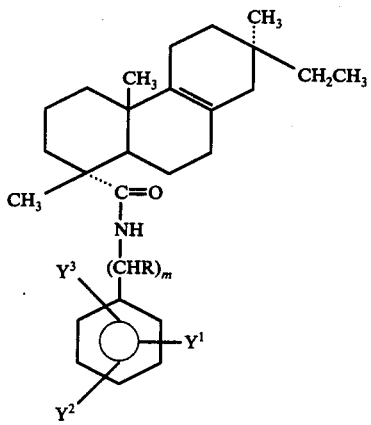

wherein
R is hydrogen or lower alkyl;
$m$ is 0 or 1; and each of $Y^1$, $Y^2$ and $Y^3$ independently of the other is hydrogen, lower alkyl, lower alkoxy, carboxy, carbo(lower alkoxy), hydroxy, trifluoromethyl or halogeno.

2. A compound according to claim 1 wherein $m$ is 0.
3. A compound according to claim 1 wherein R is hydrogen and $m$ is 1.
4. A compound according to claim 1 selected from the group consisting of N-(2-ethylphenyl)-Δ⁸-dihydropimaramide, Δ⁸-dihydropimaranilide, N-(2,6-dimethylphenyl)-Δ⁸-dihydropimaramide, N-(2,4,6-trimethylphenyl)-Δ⁸-dihydropimaramide, N-(2,6-diisopropylphenyl-Δ⁸-dihydropimaramide, N-(4-ethoxyphenyl)-Δ⁸-dihydropimaramide, N-(2-methyl-5-chlorophenyl)-Δ⁸-dihydropimaramide, N-(3-trifluoromethylphenyl)-Δ⁸-dihydropimaramide, N-(3-hydroxy-4-carboxyphenyl)-Δ⁸-dihydropimaramide, N-(4-methoxycarbophenyl)-Δ⁸-dihydropimaramide, N-(3,4-dichlorophenyl)-Δ⁸-dihydropimaramide, N-α-n-pentylbenzyl-Δ⁸-dihydropimaramide, N-α-methylbenzyl-Δ⁸-dihydropimaramide, N-(4-methoxybenzyl)-Δ⁸-dihydropimaramide, N-benzyl-Δ⁸-dihydropimaramide, N-(4-methylbenzyl)-Δ⁸-dihydropimaramide, N-(2-chlorobenzyl)-Δ⁸-dihydropimaramide, N-Δ-ethylbenzyl-Δ⁸-dihydropimaramide and N-(3-methoxyphenyl)-Δ⁸-dihydropimaramide.

5. A serum cholesterol reducing and antiphlogistic pharmaceutical composition comprising an effective amount of a compound according to claim 1 in combination with a pharmaceutical carrier.

6. The method of reducing serum cholesterol in humans and other animals comprising administering thereto an effective amount of a compound according to claim 1.

7. The method of achieving an antiphlogistic effect in humans and other animals which comprises administering thereto an effective amount of a compound according to claim 1.

* * * * *